United States Patent
Sokel et al.

(10) Patent No.: US 10,478,324 B2
(45) Date of Patent: Nov. 19, 2019

(54) HANDLE FOR MEDICAL DEVICE DEPLOYMENT

(71) Applicant: W. L. Gore & Associates, Inc., Newark, DE (US)

(72) Inventors: Justin W. Sokel, Flagstaff, AZ (US); Adam T. Storey, Seattle, WA (US); Jared L. Van Cleave, Kirkland, WA (US)

(73) Assignee: W. L. Gore & Associates, Inc., Newark, DE (US)

( * ) Notice: Subject to any disclaimer, the term of this patent is extended or adjusted under 35 U.S.C. 154(b) by 624 days.

(21) Appl. No.: 14/822,870

(22) Filed: Aug. 10, 2015

(65) Prior Publication Data

US 2016/0045348 A1 Feb. 18, 2016

Related U.S. Application Data

(60) Provisional application No. 62/036,513, filed on Aug. 12, 2014.

(51) Int. Cl.
*A61F 2/966* (2013.01)
*A61F 2/95* (2013.01)

(52) U.S. Cl.
CPC ...... *A61F 2/966* (2013.01); *A61F 2002/9517* (2013.01); *A61F 2002/9665* (2013.01)

(58) Field of Classification Search
CPC ......... A61F 2002/9517; A61B 17/2841; A61B 17/2909; A61B 1/0052
USPC ...................................................... 623/1.11
See application file for complete search history.

(56) References Cited

U.S. PATENT DOCUMENTS

| | | | |
|---|---|---|---|
| 5,620,458 A | 4/1997 | Green et al. | |
| 6,203,550 B1 | 3/2001 | Olson | |
| 6,352,561 B1 | 3/2002 | Leopold et al. | |
| 6,551,330 B1 * | 4/2003 | Bain | A61B 17/0469 606/144 |
| 6,733,521 B2 | 5/2004 | Chobotov et al. | |

(Continued)

FOREIGN PATENT DOCUMENTS

| | | |
|---|---|---|
| EP | 1474074 B1 | 4/2004 |
| EP | 1441668 B1 | 1/2008 |

(Continued)

OTHER PUBLICATIONS

International Search Report and Written Opinion for PCT/US2015/044584 dated Nov. 17, 2015, corresponding to U.S. Appl. No. 14/822,870, 5 pages.

*Primary Examiner* — Diane D Yabut
*Assistant Examiner* — Majid Jamialahmadi

(57) ABSTRACT

A delivery system for endoluminal delivery of an expandable device comprising a catheter having a proximal end and an opposite distal end configured to support an expandable device, a primary sheath having a delivery position in which the primary sheath constrains the expandable device toward a collapsed configuration suitable for endoluminal delivery, and a handle having an actuator for axially displacing the primary sheath from the delivery position, wherein the handle includes a knob for operating one or more functions of the handle which is initially hidden to prevent use by a user and then revealed as a result of displacement of the primary sheath from delivery position so as to allow subsequent actuation of the knob by the user.

20 Claims, 7 Drawing Sheets

(56) References Cited

U.S. PATENT DOCUMENTS

| | | |
|---|---|---|
| 6,911,039 B2 | 6/2005 | Shiu |
| 6,974,471 B2 | 12/2005 | Van Schie |
| 7,029,488 B2 | 4/2006 | Schonholz et al. |
| 7,081,132 B2 | 7/2006 | Cook |
| 7,147,661 B2 | 12/2006 | Chobotov |
| 7,655,034 B2 | 2/2010 | Mitchell et al. |
| 7,789,860 B2 | 9/2010 | Brady et al. |
| 7,837,724 B2 | 11/2010 | Keeble |
| 7,938,851 B2 | 5/2011 | Olson |
| 7,967,829 B2 | 6/2011 | Gunderson |
| 7,976,575 B2 | 7/2011 | Hartley |
| 8,167,927 B2 | 5/2012 | Chobotov |
| 8,241,346 B2 | 8/2012 | Chobotov |
| 8,257,431 B2 | 9/2012 | Henderson |
| 8,262,671 B2 | 9/2012 | Osypka |
| 8,328,861 B2 | 12/2012 | Martin |
| 8,361,135 B2 | 1/2013 | Dittman |
| 8,480,725 B2 | 7/2013 | Rasmussen |
| 8,968,384 B2 | 3/2015 | Pearson |
| 9,060,895 B2 | 6/2015 | Hartley |
| 9,132,025 B2 | 9/2015 | Aristizabal |
| 9,254,204 B2 | 2/2016 | Roeder |
| 9,308,349 B2 | 4/2016 | Rezac |
| 9,498,361 B2 | 11/2016 | Roeder |
| 9,585,743 B2 | 3/2017 | Cartledge |
| 9,585,774 B2 | 3/2017 | Aristizabal |
| 9,675,485 B2 | 6/2017 | Essinger |
| 9,681,968 B2 | 6/2017 | Goetz |
| 9,700,701 B2 | 7/2017 | Benjamin |
| 9,782,284 B2 | 10/2017 | Hartley |
| 9,937,070 B2 | 4/2018 | Skelton |
| 2004/0138734 A1 | 7/2004 | Chobotov et al. |
| 2005/0080476 A1 | 4/2005 | Gunderson et al. |
| 2005/0283223 A1 | 12/2005 | Greenan |
| 2006/0173524 A1 | 8/2006 | Salahieh et al. |
| 2013/0261726 A1* | 10/2013 | Alger .................. A61F 2/95 623/1.11 |
| 2013/0267995 A1 | 10/2013 | Voss et al. |
| 2014/0128844 A1 | 5/2014 | Kornowski et al. |
| 2017/0172724 A1 | 6/2017 | Cartledge |
| 2017/0281382 A1 | 10/2017 | Lostetter |

FOREIGN PATENT DOCUMENTS

| | | |
|---|---|---|
| EP | 1915113 B1 | 3/2010 |
| EP | 1358903 B1 | 2/2011 |
| EP | 2421481 | 2/2012 |
| EP | 2749251 B1 | 7/2016 |
| EP | 2956198 B1 | 11/2017 |
| WO | 2010/123664 | 10/2010 |
| WO | 2014/55765 | 4/2014 |
| WO | 2015/153375 | 10/2015 |

* cited by examiner

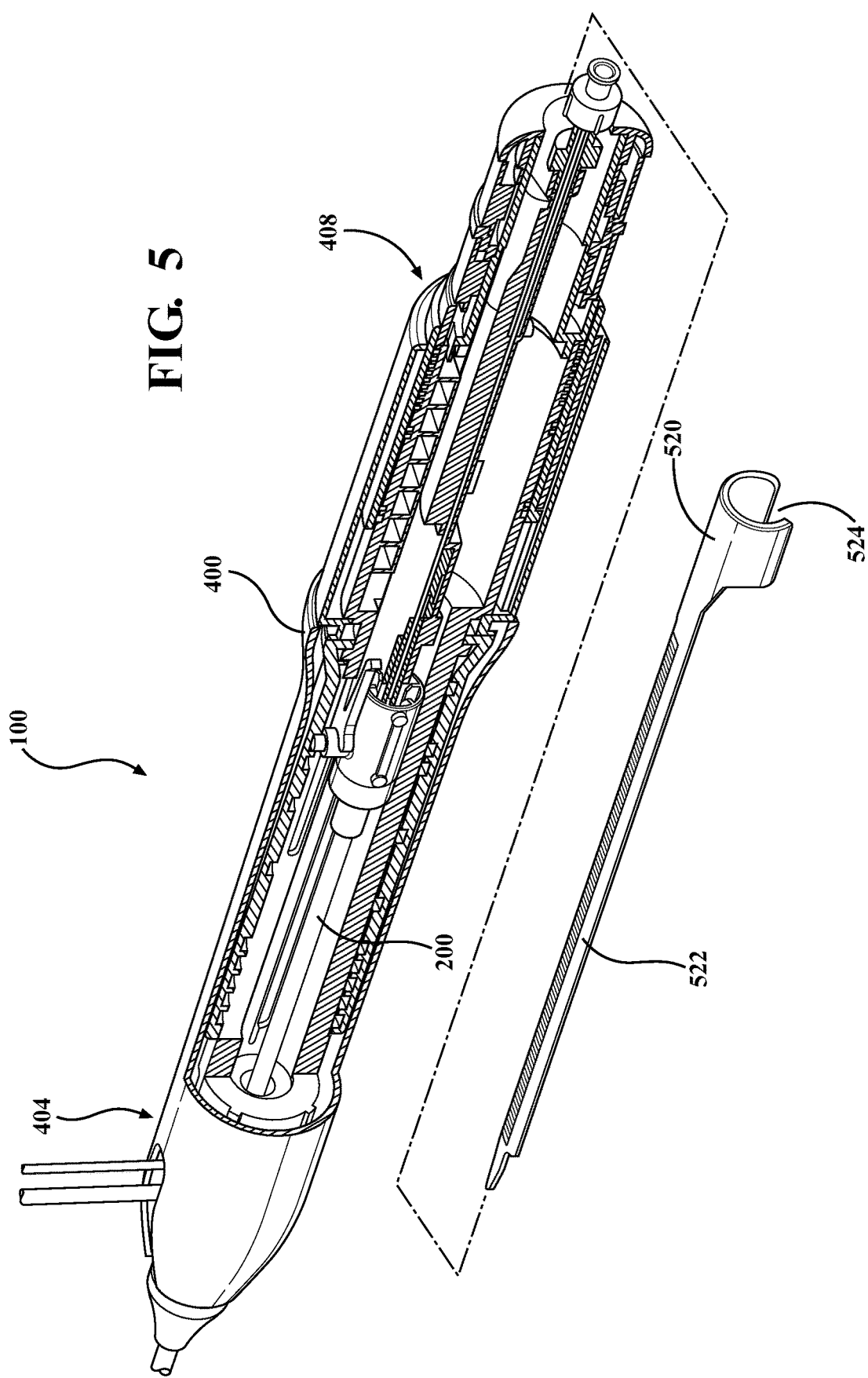

HANDLE FOR MEDICAL DEVICE DEPLOYMENT

BACKGROUND

Field

The present disclosure relates to handles for medical device deployment systems and, more particularly, to handles configured for use in multi-stage deployment systems for expandable medical devices.

Discussion

Handles for catheter-based deployment systems for endoluminal delivery of expandable devices are well-known in the art. It remains desirable to provide improved handles that can accommodate multi-stage endoluminal delivery and deployment of expandable medical devices, while improving or at least maintaining ease of operation to the clinician.

BRIEF DESCRIPTION OF THE DRAWINGS

The accompanying drawings are included to provide a further understanding of the present disclosure and are incorporated in and constitute a part of this specification, illustrate embodiments of the present disclosure and together with the description serve to explain the principles of the present disclosure.

FIGS. 1-5 are cutaway perspective views of a deployment handle for a medical device delivery system, shown in successive stages of use.

DETAILED DESCRIPTION

A handle mechanism is disclosed herein for use in connection with delivery systems for endoluminal delivery and deployment of medical devices, such as vascular endoprosthetic implants. A delivery system in accordance with the present disclosure can include a first actuator for selectively actuating a first tubular member and a second actuator for selectively actuating a second tubular member, wherein the second actuator is initially hidden and subsequently presented for use in response to operation of the first actuator.

Referring to FIGS. 1-5, for example, a medical device delivery system is generally indicated at 100. The delivery system 100 includes a catheter (not shown) having a proximal end and an opposite distal end. The distal end of the catheter is configured for supporting at least one expandable, endoluminally deliverable medical device (not shown). Examples of endoluminally deliverable medical devices include stents, grafts, replacement heart valves, and the like, or any combination thereof.

The delivery system can include one or more tubular members for releasably constraining the medical device for endoluminal delivery and deployment. The delivery system 100 can, for example, include an elongated first tubular member 200 having a generally cylindrically shaped side wall defining a longitudinally extending lumen (not shown). The first tubular member 200 can have a delivery configuration, in which the medical device is placed within the lumen and constrained by the side wall toward a constrained state suitable for endoluminal delivery of the medical device. The delivery system 100 can also include an elongated second tubular member 300 having a generally cylindrically shaped side wall defining a longitudinally extending lumen (not shown). In the delivery configuration, the second tubular member 300 can be disposed between the first tubular member 200 and the medical device to limit expansion of medical device following removal or displacement of the first tubular member 200 from the delivery configuration. More specifically, the second tubular member 300 can limit expansion of the medical device toward an intermediate state that is larger than the constrained state and yet still smaller than a fully-deployed state, so as to allow axial and rotational positioning of the medical device at the treatment site prior to committing to a full deployment of the medical device. Examples of tubular members include catheters, sheaths, and introducers, or any elongate, tubular member used for supporting and endoluminally delivering a medical device. The tubular members can be constructed using any suitable material or combination of materials, such as polymers, polymer films, and braided wire structures, and any suitable methods known to those having ordinary skill in the art, such as injection molding, extrusion, flow-formed layered wraps, or any combination thereof.

Figure 1:
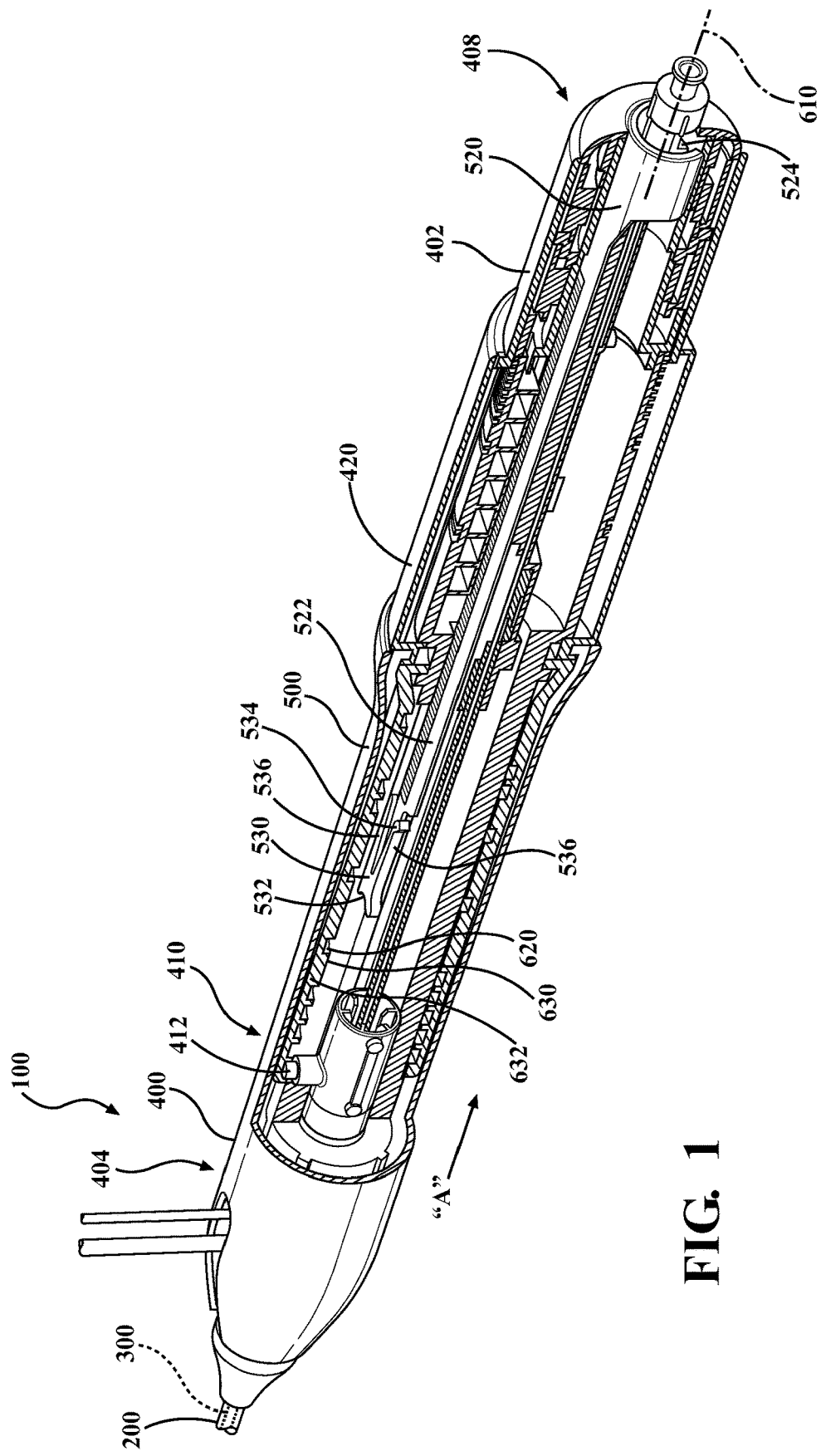
Figure 2:
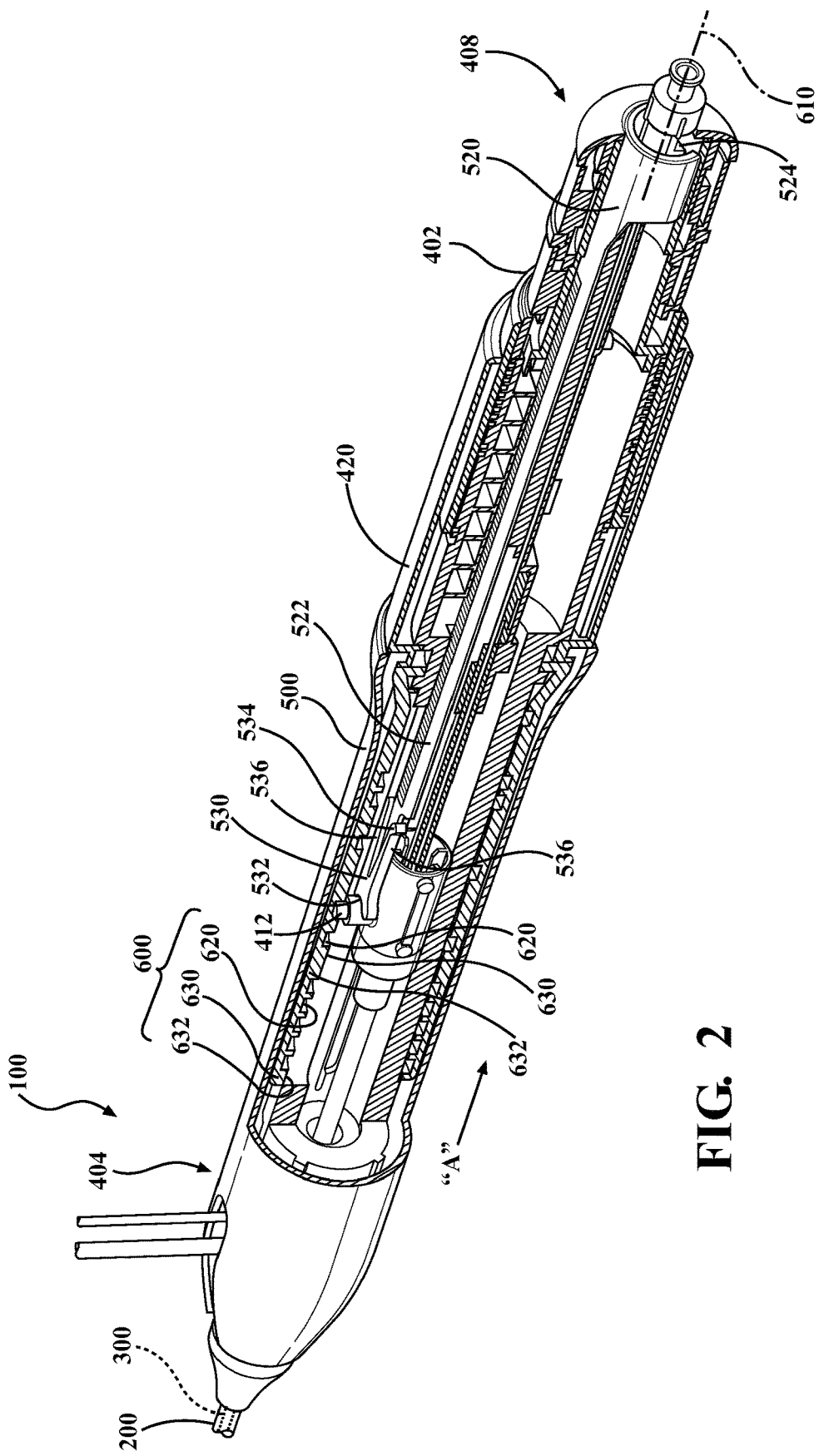
Figure 2A:
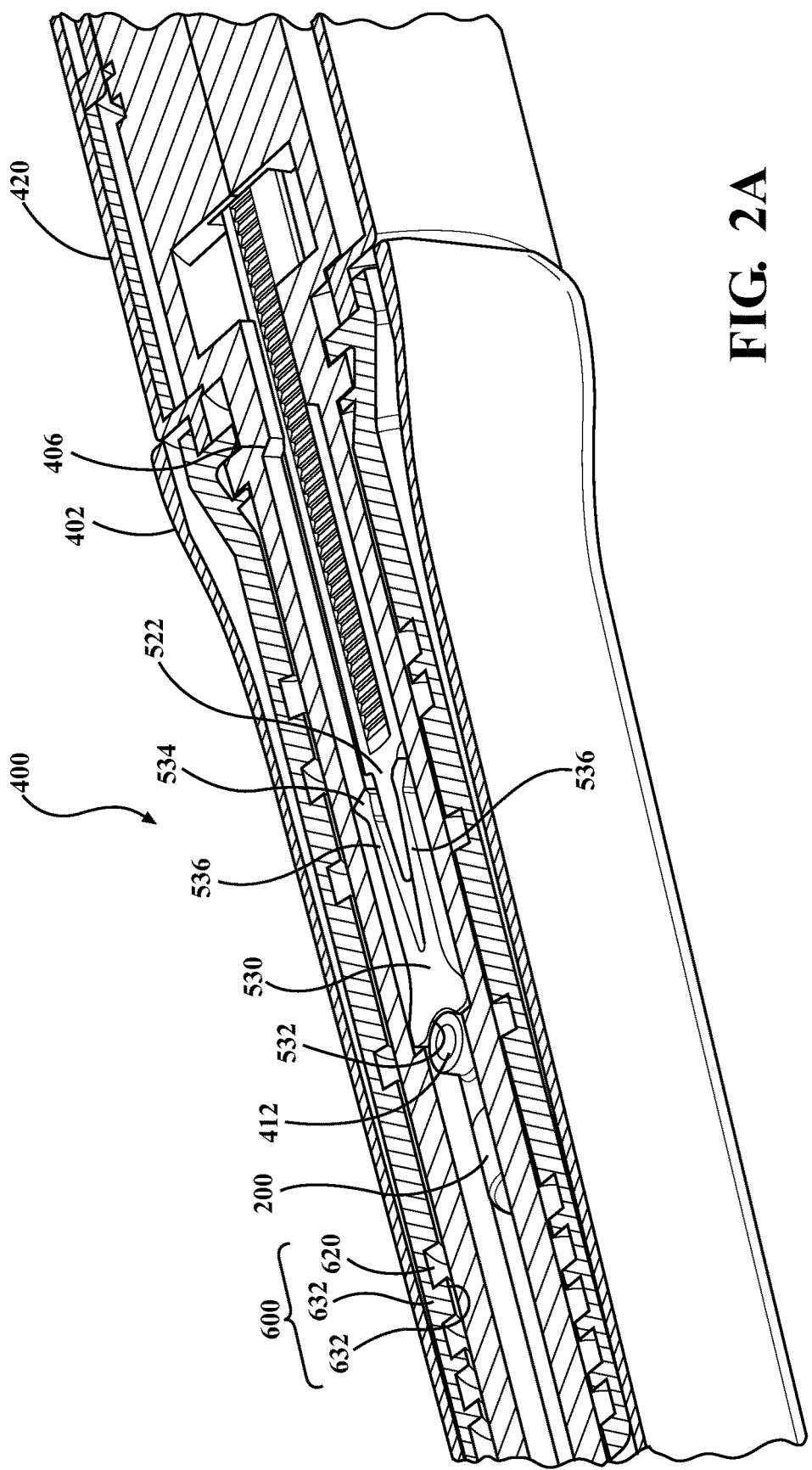
FIGS. 2A and 3A are enlarged views of FIGS. 2 and 3, respectively.
Figure 3:
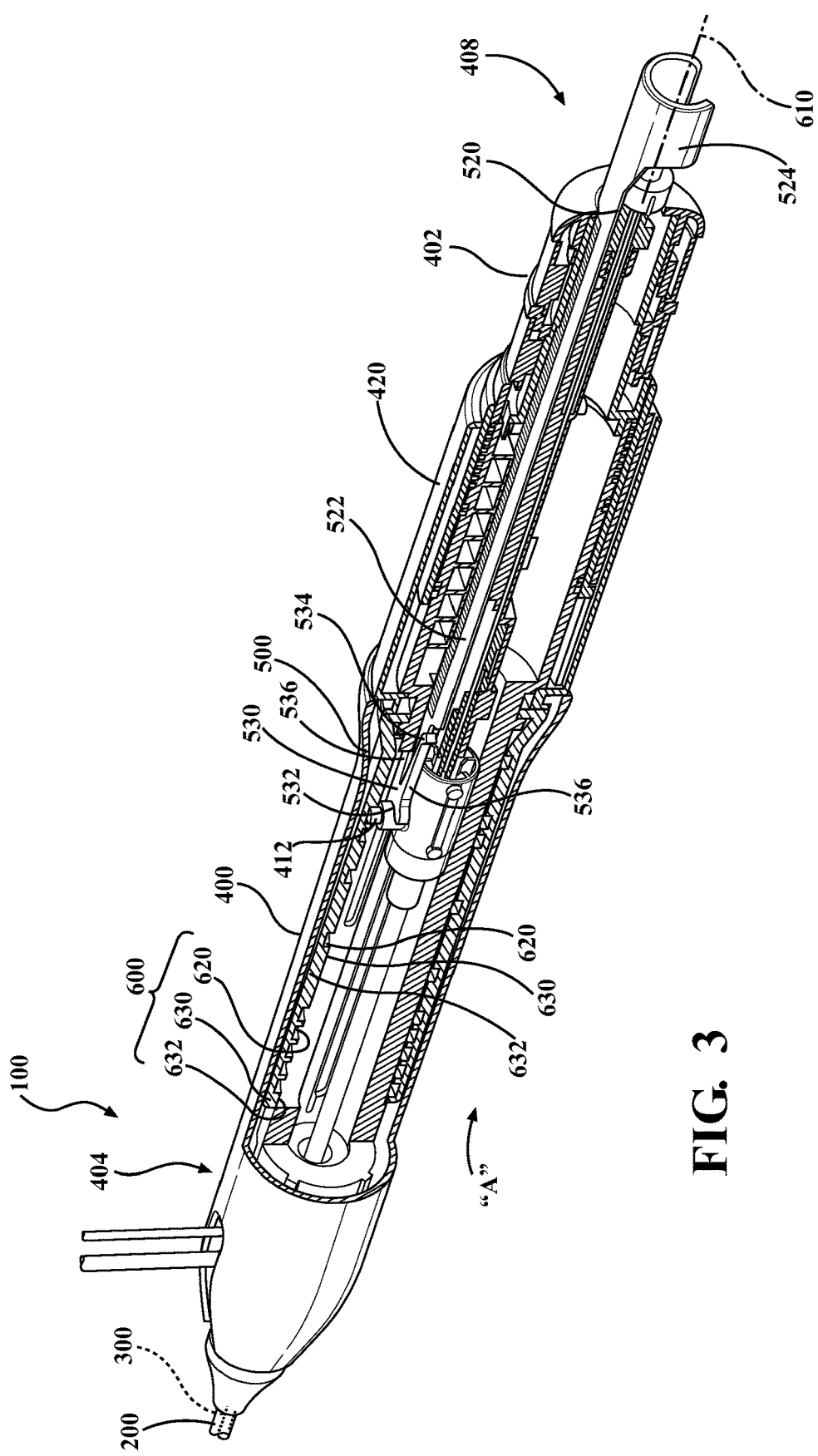
Figure 4:
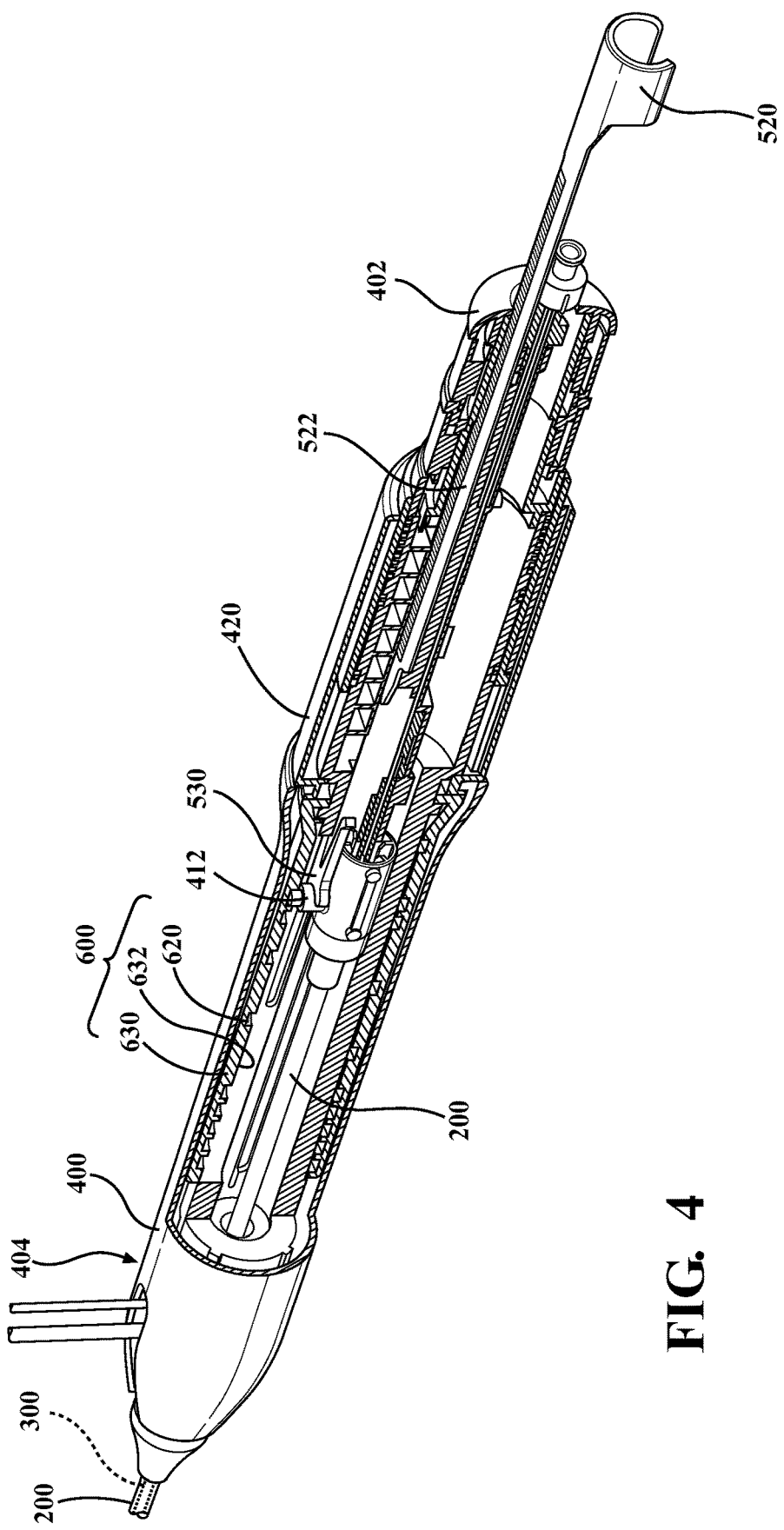

The delivery system includes a handle having actuators and interfaces, such as knobs, operable to facilitate displacement, removal or actuation of the first and second tubular members from their respective delivery configurations. Such a handle is disclosed in FIGS. 1-5 and generally indicated at 400. The handle 400 includes an outer housing 402. The handle 400 is disposed along and coupled to the proximal end of the catheter. The handle 400 includes a first actuator mechanism 410 and a first knob 420 for manual operation of the first actuator mechanism 410. The first actuator mechanism 410 includes a follower 412 that is axially displaceable as indicated by the arrow "A" in FIG. 1 in response to corresponding operation of the first knob 420. The follower 412 is, in turn, coupled to the first tubular member 200 to cause axial displacement of the first tubular member with the follower 412 during operation of the first knob 420. The first tubular member 200 is shown in FIG. 1 in the delivery configuration. In this configuration, the follower 412 is positioned at a distal portion 404 of the handle 400. Operation of the first knob 420 causes displacement of the first tubular member 200 with the follower 412 from the delivery configuration, as shown in FIG. 1, toward the proximal portion 408 of the handle 400, as shown in FIGS. 2-4.

Still referring to FIGS. 1-4, the handle 400 includes a second actuator mechanism 500 and a second knob 520 for manual operation of the second actuator mechanism 500. As shown in FIG. 1, with the first tubular member 200 in the delivery configuration, the second knob 520 is positioned and hidden at a proximal portion 408 of the handle 400. An arm 522 extends from the second knob 520 toward the distal portion 404 of the handle 400 for engaging the follower 412 during operation of the first actuator mechanism 410. As shown, in the delivery configuration, an end of the arm 522 can be spaced apart from the follower 412 to allow an initial displacement of the first tubular member 200 without causing corresponding displacement of the second knob 520 from the housing 402. The second knob 520 and arm 522 are supported by and slidably coupled to the housing 402 to allow displacement of the second knob 520 from the handle housing 402 during movement of the follower 412 with the first tubular member 200 between the positions shown in FIG. 1 and FIG. 3.

Optionally, a receiver 530 can be provided to support and locate the end of the arm 522 relative to the handle 400. A distal end 532 of the receiver 530 is configured to engage the follower 412 instead of the end of the arm 522, as previously discussed. The opposite proximal end 534 of the receiver 530 is defined by a pair of legs 536. The legs 536 are spaced apart to receive the end of the arm 522 therebetween.

The actuator mechanisms of the handle can include a variety of mechanisms for moving or actuating the tubular members in response to actuation of respective knobs of the handle. The first actuator mechanism 410 of the handle 400 shown in the figures, for example, includes a helically threaded positioner mechanism 600 for displacing the first tubular member 200 along an axis 610 in response to rotation of the first knob 420 about the axis 610.

The positioner mechanism 600 includes a helical slot or guide 620 formed along an inner surface 632 of a tubular wall 630 that extends from the first knob 420. The wall 630 and, therefore, the helical guide 620 rotate with the first knob 420. The follower 412 is disposed within a lumen defined by the wall 630, is engaged with the helical guide 620 and is rotatably constrained with respect to the axis 610, so that rotation of the helical guide 620 with the first knob 420 causes axial displacement of the follower 412 and the first tubular member 200 therewith, relative to the catheter and the second tubular member 300. Thus, rotation of the first knob 420 causes or allows progressive expansion of the medical device from the constrained state as the first tubular member 200 is retracted relative to the catheter from the delivery configuration of FIG. 1 to the various stages of displacement shown in FIGS. 2-3.

Figure 3A:
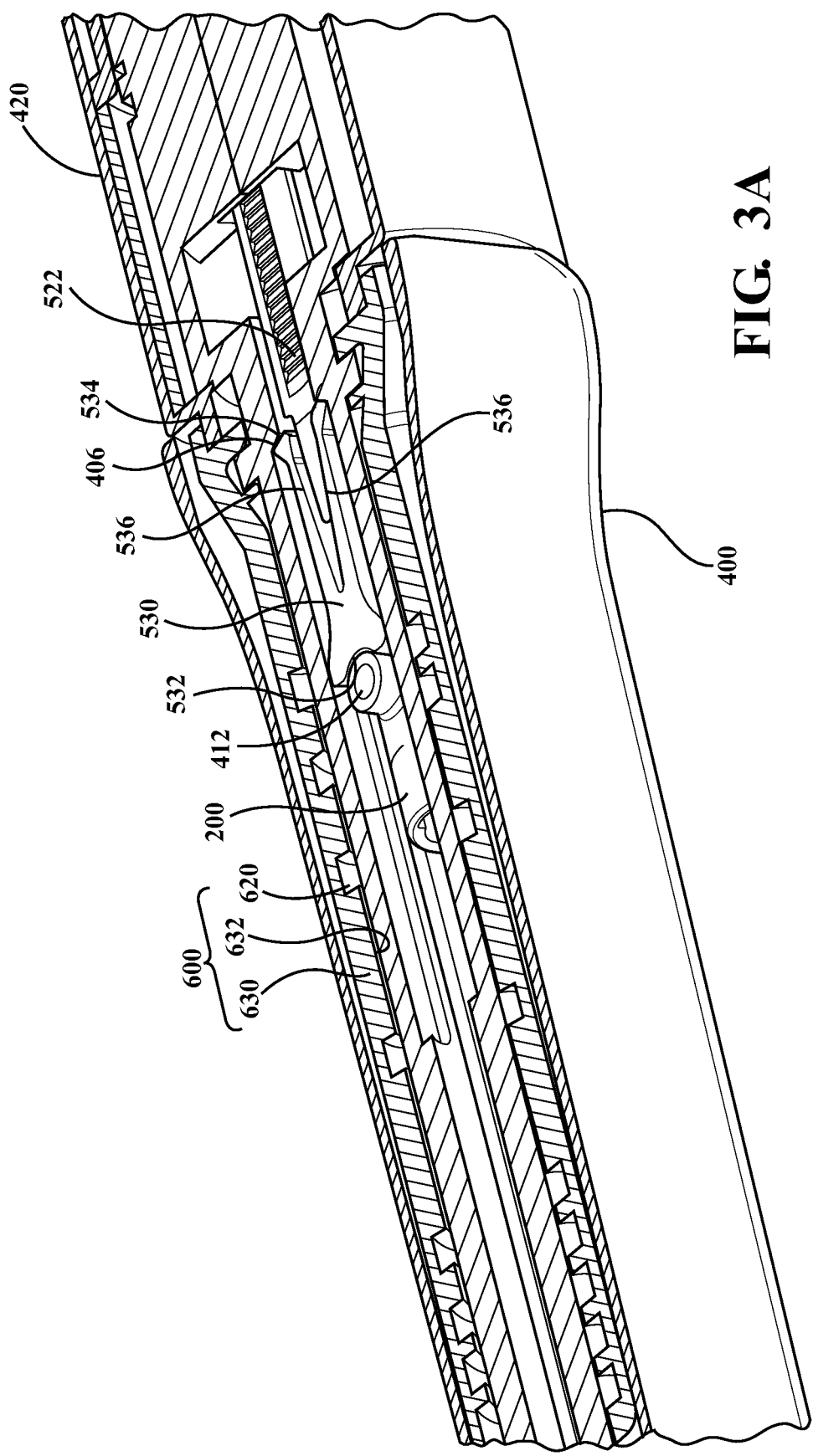

Referring to FIG. 3A, eventual engagement between the proximal end 534 of the receiver 530 and a locating surface 406 in the handle 400 provides a positive stop to prevent further axial displacement of the follower 412, first tubular member 200 and, in turn, further rotation of the first knob 420.

As earlier discussed, expansion of the medical device from the constrained state following removal of the first tubular member 200 is limited to the intermediate state by the second tubular member 300. Maintaining the medical device at the intermediate state allows axial or rotational positioning of the medical device at the treatment site prior to committing to full deployment.

The second tubular member 300 can also be axially retracted like the first tubular member. Alternatively, the second tubular member 300 can be formed from a film sleeve held together by an elongated member (not shown), such as a deployment wire or fiber. An example of the latter arrangement is disclosed in U.S. Pat. No. 6,352,561 to Leopold et al., the content of which is incorporated herein by reference in its entirety. In either case, the second actuating mechanism 500 may be provided as a coupling between the second knob 520 and the second tubular member 300 and/or the elongated member, so that removing the second knob 520 from the handle 400 causes removal and/or opening or otherwise actuation of the second tubular member 300.

In operation, the first knob 420 is rotated to actuate the threaded positioner mechanism 600 and cause displacement of the first tubular member 200 from the position in FIG. 1 toward the position in FIG. 3. As earlier discussed, the follower 412 is initially spaced apart from the end of the arm 522. Thus, the second knob 520 remains undisturbed and hidden inside the outer housing 402 near the proximal portion 408 of the handle 400 during initial actuation of the first knob 420 to prevent use of the second knob 520.

Displacement of the first tubular member 200 relative to the medical device allows the medical device to expand from the constrained state toward the second tubular member 300, which limits expansion of the medical device to the intermediate state. In this state, the clinician may choose to make final axial and/or rotational adjustments of the position of the medical device prior to full deployment of the medical device. Once the medical device is placed at a desired position at the treatment site, the clinician can continue to operate the first knob 420.

Eventually, as shown in FIG. 2, the follower 412 contacts the end of the arm 522 so that continued operation of the first knob 420 and movement of the first tubular member 200 translates into displacement of the second knob 520 from the outer housing 402, as shown in FIG. 3, wherein the second knob 520 is presented for use by the clinician. The second knob 520 and arm 522 can be removed and separated from the handle 400, as shown in FIGS. 4 and 5, to cause displacement and/or otherwise opening of the second tubular member 300 to allow expansion of the medical device toward engagement with surrounding vessel tissue.

The second knob 520 can include a slot 524 to accommodate use of a guidewire (not shown), which allows the second knob 520 to be substantially coaxial or otherwise near the axis 610.

After full deployment of the medical device, the handle 400 can be separated from the first tubular member 200 to allow the first tubular member 200 to be used as an introducer sheath for other medical devices or related surgical implements.

It will be apparent to those skilled in the art that various modifications and variations can be made in the present disclosure without departing from the spirit or scope of the present disclosure. Thus, it is intended that the present present disclosure cover the modifications and variations of this present disclosure provided they come within the scope of the appended claims and their equivalents.

What is claimed is:

1. A delivery system for endoluminal delivery of an expandable device, said delivery system comprising
a catheter having a proximal end and an opposite distal end, the distal end configured to support the expandable device;
a primary sheath having a delivery position in which the primary sheath constrains the expandable device toward a collapsed configuration suitable for endoluminal delivery;
a handle having a first actuator that is rotatable and non-translatable wherein rotation of the first actuator causes axial displacement of the primary sheath along the catheter from the delivery position, the handle having a second actuator for operating one or more functions of the handle, wherein the second actuator is initially hidden to prevent use by a user and then revealed as a result of the axial displacement of the primary sheath along the catheter from the delivery position so as to allow subsequent actuation of the second actuator by the user.

2. The delivery system as set forth in claim 1 including a secondary sheath having a delivery position in which the secondary sheath limits expansion of the expandable device to an intermediate configuration larger than a constrained configuration and smaller than a fully deployed configuration.

3. The delivery system as set forth in claim 2, wherein the one or more functions of the handle includes deployment of the secondary sheath to allow deployment of the expandable device from the intermediate configuration.

4. The delivery system as set forth in claim 3, wherein an arm is coupled to the secondary sheath, wherein removal of the second actuator from the handle causes removal of the secondary sheath and, in turn, deployment of the expandable device toward the fully deployed configuration.

5. The delivery system as set forth in claim 1, wherein the axial displacement of the primary sheath is axial displacement of the entire primary sheath.

6. The delivery system as set forth in claim 1, wherein the second actuator includes a longitudinally extending arm for engaging the primary sheath, whereby the second actuator is displaced from an initially hidden position and revealed in response to the axial displacement of the primary sheath from the delivery position.

7. The delivery system as set forth in claim 6 including a follower fixedly secured to the primary sheath for movement therewith.

8. The delivery system as set forth in claim 7 including a receiver slidably coupled to the handle, and having a first end for engaging the follower as the primary sheath moves from the delivery position and an opposite second end for engaging an end of the arm.

9. The delivery system as set forth in claim 8 wherein the receiver includes a pair of legs extending outwardly from the second end which are spaced apart to define a tapered recess that receives the end of the arm therein.

10. The delivery system as set forth in claim 8, wherein the follower and the receiver are spaced apart when the primary sheath is in the delivery position, so that the second actuator is revealed after an initial delay following at least a partial deployment of the expandable device.

11. The delivery system as set forth in claim 7, wherein the primary sheath is displaceable by actuation of a positioner mechanism, the positioner mechanism having a tubular wall having a longitudinal axis and an inner surface defining a lumen extending along the longitudinal axis, the lumen capable of receiving the primary sheath and the follower therethrough.

12. The delivery system as set forth in claim 11, wherein the inner surface includes a helically extending slot for engaging the follower, wherein rotation of the tubular wall about the longitudinal axis causes axial displacement of the primary sheath and follower along the lumen.

13. The delivery system as set forth in claim 1, wherein the second actuator includes a longitudinally extending arm for engaging the primary sheath, whereby the second actuator is displaced from an initially hidden position and revealed in response to the axial movement of the primary sheath from the delivery position.

14. The delivery system as set forth in claim 13, wherein the primary sheath is displaceable by actuation of a positioner mechanism, the positioner mechanism having a tubular wall having a longitudinal axis and an inner surface defining a lumen extending along the longitudinal axis, the lumen capable of receiving the primary sheath and a follower therethrough.

15. The delivery system as set forth in claim 14, wherein the inner surface of the positioner mechanism includes a helically extending slot for engaging the follower, wherein rotation of the tubular wall about the longitudinal axis causes axial displacement of the primary sheath and the follower along the lumen.

16. The delivery system of claim 1, wherein the second actuator is a knob.

17. A delivery system for endoluminal delivery of an expandable device, the delivery system comprising
a catheter having a proximal end and an opposite distal end, the distal end configured to support the expandable device;
a primary sheath having a delivery position in which the primary sheath constrains the expandable device toward a collapsed configuration suitable for endoluminal delivery; and
a handle having a first actuator that is rotatable and non-translatable wherein rotation of the first actuator causes axial displacement of the primary sheath from the delivery position, the handle having a second actuator for operating one or more functions of the handle, wherein the second actuator is initially hidden to prevent use by a user and then revealed as a result of the axial displacement of the primary sheath so as to allow subsequent actuation of the second actuator by the user,
wherein the second actuator is revealed after an initial delay following displacement of the primary sheath from the delivery position.

18. The delivery system of claim 17, wherein the second actuator is a knob.

19. The delivery system of claim 17, wherein the axial displacement of the primary sheath is axial displacement of the entire primary sheath.

20. A delivery system for endoluminal delivery of an expandable device, said delivery system comprising
a catheter having a proximal end and an opposite distal end, the distal end configured to support the expandable device;
a follower fixedly secured to a primary sheath for movement therewith;
the primary sheath having a delivery position in which the primary sheath constrains the expandable device toward a collapsed configuration suitable for endoluminal delivery, wherein the primary sheath is displaceable by actuation of a positioner mechanism, the positioner mechanism having a tubular wall having a longitudinal axis and an inner surface defining a lumen extending along the longitudinal axis and including a helically extending slot for engaging the follower, the lumen capable of receiving the primary sheath and the follower therethrough such that a rotation of the tubular wall about the longitudinal axis causes axial displacement of the primary sheath and follower along the lumen; and
a handle having a first actuator for axially displacing the primary sheath from the delivery position, the handle having a second actuator for operating one or more functions of the handle, the second actuator including a longitudinally extending arm for engaging the primary sheath, wherein the second actuator is displaced from initially hidden to prevent use by a user and then revealed as a result of axial displacement of the primary sheath from the delivery position so as to allow subsequent actuation of the second actuator by the user.

* * * * *